United States Patent [19]
Wang

[11] Patent Number: 5,112,938
[45] Date of Patent: May 12, 1992

[54] CYANO- AND CARBOXY-SUBSTITUTED SPIRODILACTAMS

[75] Inventor: Pen-Chung Wang, Houston, Tex.

[73] Assignee: Shell Oil Company, Houston, Tex.

[21] Appl. No.: 660,835

[22] Filed: Feb. 26, 1991

Related U.S. Application Data

[63] Continuation-in-part of Ser. No. 567,484, Aug. 18, 1990, Pat. No. 5,037,948, which is a continuation-in-part of Ser. No. 503,416, Mar. 30, 1990, abandoned.

[51] Int. Cl.$^5$ .............................................. C08G 63/20
[52] U.S. Cl. ...................................... 525/272; 538/289; 538/290; 538/291; 538/292; 538/297; 538/298; 538/300; 538/323; 538/327; 538/335; 538/87
[58] Field of Search ............... 528/272, 289, 290, 291, 528/292, 297, 298, 300, 327, 335, 87

[56] References Cited

U.S. PATENT DOCUMENTS

| | | | |
|---|---|---|---|
| 3,824,211 | 7/1974 | Howerton | 260/47 C |
| 4,595,745 | 6/1986 | Nkano et al. | 528/125 |
| 4,800,231 | 1/1989 | Wang | 560/176 |
| 4,844,834 | 7/1989 | Dellinger | 252/182.3 |
| 4,847,388 | 7/1989 | Wang | 548/410 |
| 4,866,155 | 9/1989 | Mueller et al. | 528/191 |
| 4,927,906 | 5/1990 | Wang | 528/228 |
| 4,933,423 | 6/1990 | Wang | 528/96 |

OTHER PUBLICATIONS

Pariza et al, Synthetic Comm. vol. 13(3) pp. 243–254 (1983).
Cata et al, J. Amer. Chem. Soc. 77, 6022 (1955).
Cata et al, J. Amer. Chem. Soc. 79, 1706 (1957).
Sikes et al, Meeting Am. Chem. Soc. Apr. 1988, p. 614.

*Primary Examiner*—John Kight, III
*Assistant Examiner*—Sam A. Acquah

[57] ABSTRACT

Novel polyesters or polyamides are produced from a class of cyano-, cyanoalkyl-, carboxy- or carboxyalkylaryl-substituted 1,6-diaza [4,4] spirodilactams, having a cyano-, cyanoalkyl-, caroboxy- or carboxyalkylaryl substituent attached to each spiro ring nitrogen atom.

26 Claims, No Drawings

CYANO- AND CARBOXY-SUBSTITUTED SPIRODILACTAMS

CROSS-REFERENCE TO RELATED APPLICATIONS

This application is a continuation-in-part of Ser. No. 567,484, filed Aug. 18, 1990, now U.S. Pat. No. 5,037,948, which is a continuation-in-part of Ser. No. 503,416, filed Mar. 30, 1990, now abandoned.

FIELD OF THE INVENTION

This invention relates to polyesters and polyamides produced from a novel class of spirodilactams having cyano- or carboxy-containing moieties on aryl substituents on the spiro ring nitrogen atoms.

BACKGROUND OF THE INVENTION

Cyano- and carboxyaryl compounds are well-known classes of compounds that can be used as starting materials to make polyester and polyamide polymers, having a variety of uses.

On some occasions, the polyester and polyamide products which provide the more desirable properties, particularly in high temperature applications, are produced from derivatives of aromatic carboxy-terminated compounds wherein some or all of the rings share common atoms with other rings of a polycyclic structure.

It would be of advantage to provide a novel class of cyano- and carboxy compounds having a plurality of rings within the molecular structure and have such derivatives be used to produce polyester and polyamide polymers.

SUMMARY OF THE INVENTION

The present invention relates to certain polyesters and polyamides produced from a novel class of cyano-, cyanoalkyl-, carboxy- or carboxyalkylaryl-substituted [4.4] spirodilactams, including from 1,6-diazaspiro[4.4]nonane-2,7-diones having cyano-, cyanoalkyl-, carboxy- or carboxyalkylaryl substituents on the ring nitrogen atoms of the spirodilactam ring system.

DESCRIPTION OF THE INVENTION

The novel precursors of the polymers of the invention are cyano-, cyanoalkyl-, carboxy- or carboxyalkylaryl-substituted 1,6-diazaspiro[4.4]nonane-2,7-dione having the cyano-, cyanoalkyl-, carboxy- or carboxyalkylaryl substituents on the spiro ring nitrogen atoms and optionally having acyclic or cyclic substituents in the 3-, 4-, 8- and 9-positions of the spiro ring system.

Accordingly, the invention is directed to polymers produced from a cyano-, cyanoalkyl-, carboxy- or carboxyalkylaryl-substituted spirodilactam comprising a spirodilactam compound having nitrogen atoms in the 1- and 6-positions of the spiro ring system and having a cyano-, cyano-alkyl-, carboxy- or carboxyalkylaryl substituent on each spiro ring nitrogen atom, the spirodilactam compound having up to about 60 carbon atoms. As generically used herein, "carboxyaryl" or "carboxyalkylaryl" means an aryl or alkylaryl group substituted by a carboxylic acid group —C(O)OH or by a functional derivative of said carboxy moiety selected from acid chlorides and bromides, anhydrides, amides, esters or salts.

The substituted spirodilactam of the invention includes those of the formula I

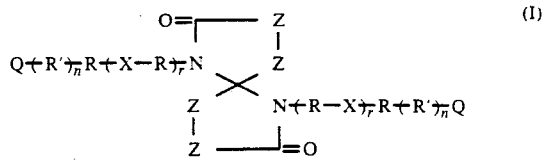

wherein Q is —CN or is —C(O)Y in which Y is chlorine or bromine, or Y is OY' in which Y' is hydrogen, a salt-forming cation or an unsubstituted or inertly substituted aliphatic or aromatic group of from 1 to 20 carbon atoms, or Y is N(Y")$_2$ in which each Y" independently is a hydrogen atom or an unsubstituted or inertly substituted aliphatic or aromatic group of from 1 to 20 carbon atoms, Z is independently >C(Z') in which Z' independently is hydrogen, lower alkyl of up to 4 carbon atoms, preferably methyl, halogen, preferably the lower halogens, fluoro or chloro, or aryl, preferably phenyl, or Z is such that the two adjacent Z groups, taken together form a ring system Z" of 1 to 3 rings, each ring having from 5 to 7 ring atoms, up to two of which are heteroatoms selected from nitrogen atoms, oxygen atoms or sulfur atoms with the remainder of the ring atoms being carbon atoms, there being up to 15 carbon atoms in each Z", two of which ring carbon atoms form a bridge between the two carbon atoms (spiro and carbonyl carbon atoms) connected by the adjacent Z groups. In the above formula I, R independently is an aromatic group of up to 18 carbon atoms which can have up to 4, preferably up to 2, aromatic rings, inclusive; R' is an aliphatic group of up to 10 carbon atoms, inclusive. Each of R and R' is hydrocarbyl, i.e., contains only atoms of carbon and hydrogen, or is substituted hydrocarbyl containing additional atoms in the form of inert substituents, such as halogen, preferably the middle halogens, chlorine or bromine. The terms n and r in the above formula I are each independently 0 or 1 and X is a direct valence bond or X is alkylene of up to 8 carbon atoms, inclusive, oxy, thio, sulfonyl, carbonyl, dioxyphenylene, 2,2-di(oxyphenyl)propane, dioxyphenyl sulfone or dioxydiphenylene.

When Y' is a salt-forming cation, it is selected from alkali metals, alkaline earth metals, aluminum, heavy metals, such as copper, silver, nickel and the like, ammonia or a tetrahydrocarbylammonium compound in which the total number of carbon atoms in the hydrocarbyl groups is between 4 and 70 carbon atoms. The hydrocarbyl groups can be alkyl, aryl, aralkyl and the like. Preferably, the hydrocarbyl groups are selected from alkyl groups containing from 1 to 10 carbon atoms and aralkyl groups containing from 7 to 10 carbon atoms.

Q is preferably —C(O)Y in which Y is chlorine, OY' in which Y' is hydrogen or alkyl of from 1 to 4 carbon atoms, e.g., methyl or ethyl, or N(Y")$_2$ in which each Y" is a hydrogen atom.

Spirodilactams of a considerable variety of structures are included in the compounds of the invention. In the embodiment of the invention wherein Q is —C(O)OH and the moieties of the above compounds of the formula I are not part of a fused ring system and are therefore acyclic, i.e., Z is >C(Z')$_2$, the spirodilactam is illustrated by 1,6-di(4-carboxyphenyl)-1,6-diazaspiro[4.4]nonane-2,7-dione, 1,6-di(3-carboxy-4-chlorophenyl)-3,8-dimethyl-1,6-diazapiro[4.4]-nonane-2,7-dione, 1,6-di(3-carboxyphenyl)-3,8-diphenyl-1,6-diazaspiro[4.4-

]nonane-2,7-dione, 1,6-di[4-(4-carboxybenzyl)phenyl]-1,6-diazaspiro[4.4]nonane-2,7-dione, 1,6-di(4-carboxyphenyl)-3,3,4,4,8,8,9,9-octamethyl-1,6-diazaspiro[4.4]nonane-2,7-dione, 1,6-di[4-(4'-carboxybiphenyl)]-3,3-dimethyl-1,6-diazaspiro[4.4]nonane-2,7-dione, 1,6-di(4-carboxymethylphenyl)-1,6-diazaspiro[4.4]nonane-2,7-dione, 1,6-di[2-(4-carboxyphenyl)propyl]1,6-diazaspiro[4.4]nonane-2,7-dione, 1,6-di[4-(4-carboxyphenylisopropyl)phenyl]-1,6-diazaspiro[4.4]nonane-2,7-dione and the like. In the embodiment wherein Q is —C(O)OH, and the adjacent Z moieties on each ring form a cyclic structure fused to the spiro ring system, illustrative spirodilactams include 1,6-di(4-carboxyphenyl)-3,4,8,9-dibenzo-1,6-diazaspiro[4.4]nonane-2,7-dione, 1,6-di(4-carboxymethylphenyl)-3,4,8,9-dibenzo-1,6-diazaspiro[4.4]nonane-2,7-dione, 1,6-di[4-(4-carboxyphenyl)phenyl]-3,4,-8,9-dipyrido-1,6-diazaspiro[4.4]nonane-2,7-dione and 1,6-di[4-(4-carboxyphenyloxy)phenyl]-3,4,8,9-di(cyclopentano)-1,6-diazaspiro[4.4]nonane-2,7-dione and the like. Also suitable are those spirodilactams wherein one spiro ring has a fused ring substituent and the other spiro ring is free of fused ring substituents, e.g., 1,6-di(4-carboxyphenyl)-3,4-benzo-8-methyl-1,6-diazaspiro[4.4]nonane-2,7-dione, 1,6-di[1-(4-carboxynaphthyl)]-3,4-cyclo-hexano-1,6-diazaspiro[4.4]nonane-2,7-dione and the like.

Of course, the corresponding compounds of formula I, wherein the —C(O)OH group in the above-named compounds is replaced by the corresponding anhydride, salt, ester or amide of the acid or by the acid chloride or bromide or Q is —CN, are also illustrative of the compounds of the invention.

In general, compounds of the above formula I wherein R is aromatic and hydrocarbyl are preferred, especially such compounds wherein each n and r is zero. The class of 1,6-di(carboxyphenyl) spirodilactam compounds is particularly preferred. Within the spirodilactam portion of the compounds of formula I spirodilactam rings which are substituted with hydrogen or methyl or fused with benzo rings are generally preferred, particularly the 1,6-diazaspiro[4.4]nonane-2,7-dione compounds.

The carboxyaryl-substituted spirodilactam derivatives of the above formula I are prepared by reaction of at least one "Q"-containing primary amino compound and a spirodilactam precursor. In terms of the spirodilactam of the above formula I, the "Q"-containing primary amino compound is represented by the formula II

  (II)

wherein Q, R, R', X and r have the previously stated meanings; m is 0 or 1 and HY is an acid which forms a salt with the amine, including both inorganic and organic acids which do not interfere with the reaction, such as hydrohalogenic acids, for example, hydrochloric and hydrobomic; sulfur acids, for example, surfuric or sulfonic; phosphorus acids, for example phosphoric or phosphonic; and carboxylic acids, for example, oxalic and the like. Preferably, Y is halogen, e.g., fluorine, chlorine, bromine or iodine and especially chlorine or bromine. Examples of compounds of formula II include 4-aminobenzonitrile, 4-aminobenzoic acid, 4-aminobenzoic acid chloride, methyl 4-aminobenzoate, p-aminophenylacetic acid, p-aminophenylacetonitrile or salts thereof and the like. Such amines are known in the art as, for example, aminobenzoic acids as in U.S. Pat. No. 4,844,834, or are prepared by known techniques.

The spirodilactam precursor is a 4-oxoheptanedioic acid compound or a 1,6-dioxospiro[4.4]nonane-2,7-dione. In terms of the spirodilactam of the above formula I, the 4-oxoheptanedioic acid compound spirodilactam precursors are represented by the formula III

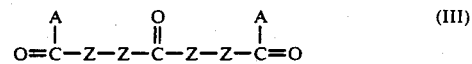  (III)

wherein Z has the previously stated meaning and A is hydroxy, lower alkoxy or halo, preferably middle halo.

When the Z moieties are linked together to form a ring system the ring system is aromatic, cycloaliphatic or heterocyclic and is hydrocarbyl containing only atoms of carbon and hydrogen besides any heteroatoms or substituted hydrocarbon containing additional atoms such as halogen, preferably middle halogen, in the form of inert carbon atom substituents.

In one embodiment employing the ketodiacid compound spirodilactam precursor, each Z moiety is >C(Z')$_2$ and the ketodiacid compound is an 4-oxoheptanedioic acid compound. In one such embodiment, largely because of a particularly convenient method of producing the spirodilactam precursor, a preferred 4-oxoheptanedioic acid compound has at least one hydrogen on the carbon atom adjacent to each carboxy function, that is, at least one Z' on each carbon atom adjacent to a carboxy function is hydrogen. Such 4-oxoheptanedioic acid compounds are represented by the formula IIIa

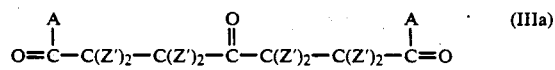  (IIIa)

wherein Z' and A have the previously stated meanings. Such 4-oxoheptanedioic acid compounds include 4-oxoheptanedioic acid, dimethyl 4-oxoheptanedioate, 2,6-dimethylheptanedioic acid, 2,3,5,6-tetramethyl-4-oxoheptanedioyl chloride, di-n-propyl 2,6-di-n-butyl-4-heptanedioate, 7-carbomethoxy-3,3,5,5-tetramethyl-4-oxohexanoic acid and the like. The preferred ketodiacids of the above formula IIIa are those wherein each Z' is hydrogen or methyl, especially hydrogen, and each A is hydroxy or methoxy, especially hydroxy.

These ketodiacid compounds are known compounds or are produced by known methods, but the esters of formula IIIa, i.e., the compounds wherein A is alkoxy, are produced by reaction of formaldehyde with an α,β-ethylenically unsaturated carboxylic acid ester such as methyl acrylate, ethyl methacrylate, methyl crotonate, methyl ethacrylate, propyl 2,3-dimethylbutanoate and the like. This reaction is conducted in the presence of a catalyst system which comprises a thiazolium salt and a tertiary amine and produces the dialkyl 4-oxoheptanedioate derivative in good yield. This process is described in greater detail in U.S. Pat. No. 4,800,231, incorporated herein by reference. Conversion of the esters thereby obtained to free acids or acid halides is by conventional methods as is the general interconversion of the acids, esters or acid halides of formula IIIa.

In a second embodiment of the ketodiacid compound spirodilactam precursor, the 4-ketodiacid incorporates cyclic moieties between the keto group and the carboxy functions, i.e., two adjacent Z moieties form a fused cyclic ring structure Z". Such diacid compounds are represented by the formula IIIb.

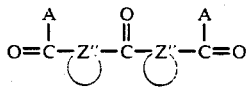
(IIIb)

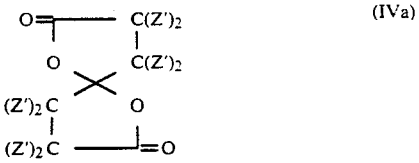
(IVa)

wherein A and Z" have the previously stated meanings. Illustrative of these cyclic ketodiacid compounds are di(2-carboxycyclohexyl) ketone, di(2-carboxyphenyl) ketone, di(2-carbopropoxycyclo-4-pentenyl) ketone, di(2-chlorocarbonylphenyl) ketone, di(2-carboxypyridyl) ketone, 2-carboxyphenyl N-methyl-3-carboxy-2pyrryl ketone, di(3-carbethoxy-2-morpholyl) ketone, di(3-carbomethoxy-2-napthyl) ketone and the like. The preferred cyclic ketodiacid compounds of formula IIIb are those wherein each Z" is a ring system of from 5 to 6 carbon atoms, inclusive, and up to one nitrogen atom, particularly benzo.

Such ketodiacids are known compounds or are produced by known methods, such as the method of U.S. Pat. No. 1,999,181 or the method of Cava et al, *J. Am. Chem. Soc.*, 77, 6022 (1955).

In yet another embodiment of the diketone compound spirodilactam precursor, the ketodiacid incorporates one fused cyclic moiety with the remainder of the Z moieties being $>C(Z')_2$, i.e., the compounds are of the formula IIIc.

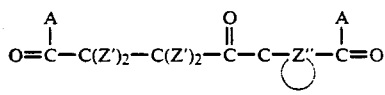
(IIIc)

wherein A, Z' and Z" have the previously stated meanings. Such ketodiacids of one cyclic moiety are illustrated by 3-(2-carboxybenzoyl)propionic acid, 3-(2-carbomethoxy-2-pyridyloyl)-2-ethylpropionic acid, ethyl 3-(2-carbethoxybenzoyl)propionate, 3-(2-carboxy-4-methylbenzoylbutyrl) chloride and the like. The ketodiacids of the above formula IIIc are known compounds or are produced by known methods. For example, 2-carboxymethylbenzaldehyde reacts with methyl acrylate according to the general teachings of U.S. Pat. No. 4,800,231, to produce methyl 3-(2-carbomethoxybenzoyl)propionate.

In another embodiment of the invention, the spirodilactam precursor is a 1,6-dioxaspiro[4.4]nonane-2,7-dione compound wherein the spiro ring system is substituted with hydrogen, alkyl or halogen, or which incorporates fused cyclic substituents which include the 3- and 4- spiro ring positions and/or the 8- and 9-spiro ring positions of the spiro ring system.

The spirodilactone spirolactam precursor, in terms of the spirodilactams of formula I, is represented by the formula IV

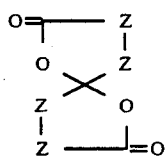
(IV)

wherein Z has the previously stated meaning.

In the embodiment of these spirodilactone spirodilactam precursors of the above formula IV wherein each Z is $>C(Z')_2$, the spirodilactone is represented by the formula IVa wherein Z' has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]nonane-2,7-dione, 4,9-diphenyl-1,6-diazaspiro[4.4]nonane-2,7-dione, 3,3,8,8-tetramethyl-1,6-dioxaspiro[4.4]nonane-2,7-dione, 3,3,4,4,8,8,9,9-octamethyl-1,6-dioxaspiro[4.4]nonane-2,7-dione, 3,4,8,9-tetrafluoro-1,6-dioxaspiro[4.4]-nonane-2,7-dione and the like. The preferred spirodilactones of the above formula IVa are those wherein at least one Z' of each Z'-substituted carbon atom is hydrogen.

The compounds of formula IVa are known compounds or are produced by known methods such as the process of Pariza et al, *Synthetic Communications*, Vol. 13(3), pp. 243-254 (1983), herein incorporated by reference.

In the embodiment of the spirodilactone spirodilactam precursors of the above formula IV which incorporates a fused cyclic moiety as a part of the two rings of the spiro ring system, the spirodilactones are represented by the formula IVb.

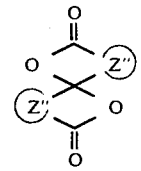
(IVb)

wherein Z" has the previously stated meaning. Typical compounds of this formula IVb are 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di(4-methylbenzo)-1,6-dioxaspiro[4.4]nonane-2,7-dione, 3,4,8,9-di-(pyrido)-1,6-dioxaspiro[4.4]nonane-2,7-dione and the like. These compounds are known compounds or are produced by known methods, for example, the process of the above Cava et al article or by the process of U.S. Pat. No. 1,999,181.

In another embodiment of the spirodilactone spirodilactam precursor, a cyclic moiety is fused to one spiro ring and the other spiro ring is free from fused ring substituents. Such spirodilactones are represented by the formula IVc

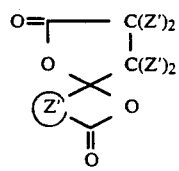
(IVc)

wherein Z' and Z" have the previously stated significance. Such spirodilactones are illustrated by 3-methyl- 8,9-benzo-1,6-dioxaspiro[4.4]nonane-2,7-dione, 3,4-benzo-1,6-dioxaspiro[4.4]nonane-2,7-dione, and 3,3,4,4-tetramethyl-8,9-morphoyl-1,6-diazaspiro[4.4]nonane-2,7-dione and the like. The spirodilactones of the above formula IVc are produced by known methods, for example, the dehydration of the corresponding ketodiacid. By way of illustration, 3,4-benzo-1,6-dioxaspiro[4.4]nonane-2,7-dione, is produced by dehydration of 3-(2-carboxybenzoyl)propionic acid through application of heat.

In general, the preferred spirodilactone spirodilactam precursors are hydrocarbon except for the oxygen atoms of the lactone moieties, and particularly preferred are those spirodilactones which are free from fused ring substituents (formula IVa) or those which have a fused ring substituent on each of the spiro rings (formula IVb). An especially preferred spirodilactone spirodilactam precursor of the first class is 1,6-dioxaspiro[4.4]-nonane-2,7-dione.

The acyclic 4-oxoheptanedioic acid compounds are known or are produced by the methods described above, but certain of the esters are also produced by the reaction of formaldehyde and unsaturated carboxylic acid esters by the process disclosed and claimed in U.S. Pat. No. 4,800,231. Interconversion of the acids, esters or acid halides of formula III is by conventional methods. The production of 4-oxoheptanedioic acid compounds of formula IV which contain cyclic moieties is by the process of Cava et al, *J. Am. Chem. Soc.*, 77, 6022 (1955). The spirodilactones of formula IIb are produced by the process of Pariza et al, *Synthetic Communications*, Vol. 13(3), pp. 243-254 (1983), or if the spirodilactones have additional fused rings by known methods including the method described by Conover et al., U.S. Pat. No. 1,999,181, Cava et al., *J. Am. Chem. Soc.*, 77, 6022 (1955), or Gourmelon et al., *Bull. Soc. Chem.* 4032 (1971). Such methods include (1) in Conover et al., the decarboxylation of dicarboxylic acid anhydrides in the presence of known decarboxylation catalysts, (2) in Cava et al., the chromic acid oxidation of cyclic (aryl) substituted dicyclic (diarylene) compounds, and (3) in Gourmelon et al., the Friedel Crafts condensation of cyclic (aryl) acid with cyclic (aryl) dicarboxylic anhydride. Other methods include Cava et al., *J. Am. Chem. Soc.*, 79, 1706 (1957) in which a fused ring-cyclobutene dibromide is treated with potassium hydroxide followed by oxidation with chromic acid in acetic acid, and Sikes et al., *Meeting Am. Chem. Soc.*, April 1988, p. 614, in which an aryl magnesium bromide having an o-tolyl group is reacted with an excess of a dicarboxylic acid anhydride in benzene-ether solution followed by oxidation with chromium (VI) oxide in glacial acetic acid. Using these methods, spirodilactones in which adjacent Z groups form a Z" ring system inertly substituted at the 3-, 3,5-, 3,4,5-or 3,4,5- and 6-positions can be prepared. Inert ring substituents include halogen, haloalkyl, alkyl, alkoxy, alkythio, tertiary-amino, tertiary-aminoalkyl, in which each alkyl group has up to 10 carbon atoms, preferably 4 carbon atoms, or aryloxy or up to 10 carbon atoms and 1 to 2 rings.

The "Q"-containing primary amino compound and the spirodilactam precursor react in a molar ratio of 2:1 although in practice reactant ratios from about 8:1 to about 1:1.5 are satisfactory. Reactant ratios of "Q"-containing primary amino compound to spirodilactam precursor which are substantially stoichiometric are preferred. Reaction is conducted in a liquid phase solution in an inert reaction diluent such as an N-alkylamide, e.g., N,N-dimethylformamide, N,N-dimethylacetamide, N-methyl-2-pyrrolidone and the like. Reaction takes place under reaction conditions at an elevated temperature, typically from about 80° C. to about 250° C., and at a reaction pressure sufficient to maintain the reaction mixture in a liquid phase, e.g., pressures up to about 20 atmospheres. Subsequent to reaction the spirodilactam product is recovered from the reaction product mixture by conventional methods such as solvent removal, precipitation and chromatographic separation and the like. Recovery of the spirodilactam product is not required, however, and particularly in cases where substantially stoichiometric quantities of reactants were employed the spirodilactam may be reacted further in situ to form Q-substituted spirodilactams of the invention.

The cyanoaryl- or cyanoalkylaryl-substituted spirodilactams in which Q in Formula I is cyano find utility as precursors of the corresponding carboxylic acid into which they are converted by conventional acid or base hydrolysis.

The spirodilactams having the carboxyaryl or carboxyalkylaryl substituents, for example, in Formula I wherein Q is —C(O)OH, or C(O)OY' wherein Y' is H or hydrocarbyl, are useful in the formation of polyester or polyamide polymers or can be converted by conventional techniques into the corresponding anhydrides, acid chlorides or bromides or salts, which also find utility in the preparation of polyester or polyamide polymers. The spirodilactams of Formula I wherein Q is —C(O)OH can be converted to the ester compounds of the invention, for example, by reaction with an appropriate hydrocarbyl halide, in the presence of triethylamine, in a solvent, such as ethyl acetate.

The spirodilactams having the carboxyaryl or carboxyalkylaryl substitutents, for example, in Formula II wherein Q is —C(O)N(Y")$_2$ and at least one Y" is hydrogen, are useful for the preparation of polyamides or can be converted by conventional techniques into the corresponding carboxylic acids. Conversely, these amides can be prepared by conventional ammonalysis from the acid or acid chloride.

In preparing polyesters, for example, 1,6-di(4-carboxyphenyl)-1,6-diazaspiro[4.4]nonane-2,7-dione or the salt, acid halide, ester or anhydride thereof is condensed with a dihydroxy compound using melt, solution or interfacial polycondensation techniques. The dihydroxy compound can be an alkylene, alicyclic or arylene dihydroxy compound, such as ethylene glycol, 1,4-butenediol, bis(4-hydroxyphenyl)methane or any of the dihydroxy compounds and methods disclosed in U.S. Pat. Nos. 4,866,155 and 3,824,211, the disclosures of which are incorporated herein by reference.

In another embodiment of polyesters, 1,6-di(4-carboxyphenyl)-1,6-diazaspiro[4.4]-nonane-2,7-dione is condensed with a diepoxide compound using conventional melt or solution polymerization techniques. The diepoxide compound can be an alkylene, alicyclic or arylene diepoxide compound, such as the diepoxides of any of the dihydroxy compounds disclosed in the above-mentioned U.S. Pat. Nos. 4,868,155 and 3,824,211. When the diepoxide compound is aliphatic, the polymerization usually takes place at room temperature and when the diepoxide compound is aromatic, the polymerization may require heating the reaction mixture, usually in the presence of a catalyst, such as a conventional acid, base or salt catalyst, to a temperature sufficient to initiate the reaction. When the molar ratio of the diepoxide compound to spirodilactam bis acid compound is essentially 1:1, a linear polyester polymer is obtained. However, when the molar ratio of diepoxide compounds to spirodilactam bis acid is greater than 1:1, a cross-linked polyester polymer is obtained.

In preparing polyamides, for example, 1,6-di(4-carboxyphenyl)-1,6-diazaspiro[4.4]nonane-2,7-dione, the amide or the acid halide thereof is reacted under conventional polymerizing conditions known in the art with an amine compound having at least two amino hydrogen substitutents using conventional conditions for the formation of polyamides. In some cases, a polymerization catalyst is used in the formation of the polyamide. The amine compound can be an aliphatic or aromatic di-primary or di-secondary amine, such as hexamethylene diamine, methylene dianiline or any of the amines and methods, disclosed in U.S. Pat. Nos. 4,595,745 and 4,933,423, or a continuation-in-part thereof, U.S. Ser. No. 474,954 filed Feb. 5, 1990, the disclosure of each being incorporated herein by reference.

The polyester products are useful for injection or compression moldings, extrusions, melt-spun or solvent-spun fibers and filaments, melt-extruded or solution-cast films, coatings and paints.

The polyamide products are useful for films, fibers, yarns and the like.

The polyester and polyamide products comprising (a) moieties derived from a spirodilactam compound, said compound having nitrogen atoms in the 1- and 6-positions of the spiro ring system and having a carboxyaryl or carboxyalkylaryl substituent on each spiro ring nitrogen atom alternating with (b) moieties derived from a dihydroxy compound, a diepoxide compound or from a primary diamine compound. For example, a polyester of the invention includes polyesters of the formula Va or Vb

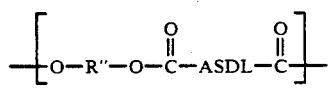
(Va)

or

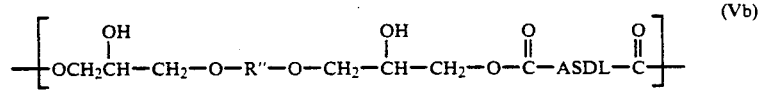
(Vb)

and polyamides of the formula VI

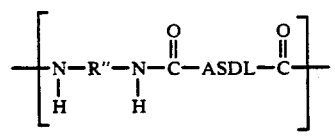
(VI)

wherein ASDL is a moiety of an aryl or alkylaryl-substituted 1,6-diaza [4.4] spirodilactam having aryl or alkylaryl substituents on each spiro nitrogen atom and R" is an unsubstituted or inertly substituted aliphatic or aromatic group of up to 18 carbon atoms. The group ASDL is represented by the removal of both Q moieties from the compounds of formula I. In the polyesters and polyamides R" is preferably an alkylene group of 2 to 10 carbon atoms or an arylene group of 6 to 10 carbon atoms.

The polyester and polyamides are polymers having a molecular weight of from about 1,000 to about 100,000, preferably from about 10,000 to about 50,000.

The invention is further illustrated by the following Illustrative Embodiments which should not be construed as limiting the invention.

ILLUSTRATIVE EMBODIMENT I

A mixture of 6.60 g (0.04 mole) of ethyl p-aminobenzoate, 3.12 g (0.02 mole) of 1,6-dioxaspiro[4.4]nonane-2,7-dione and 50 ml of N-methyl-2-pyrrolidinone (NMP) was placed in a 250 ml round-bottomed flask equipped with a mechanical stirrer and a condenser and warmed with stirring to 160°-170° C. After keeping the reaction at 160°-170° C. for 12 hours, the mixture was cooled and NMP was removed under reduced pressure. The product was then precipitated in ether and dried in a vacuum oven. A $C^{13}$NMR analysis indicated the formation of the desired spirodilactam bis-ethyl benzoate diester product in 48% yield.

ILLUSTRATIVE EMBODIMENT II

A mixture of 13.5 g (0.03 mole) of spirodilactam bis-ethyl benzoate of Embodiment I above, 4.5 g (0.03 mole) of 1,4-butanediol, ten drops of tert-butyl titanate and 50 ml of diglyme (2-methoxyethyl ether) was heated at 150°-160° C. in a nitrogen atmosphere. Ethanol by-product was removed by distillation. After the reaction was complete, the reaction mixture was poured into methanol to isolate the desired polyester polymer. Confirmation of the repeating polyester unit was made by IR and $C^{13}$NMR spectral analyses.

ILLUSTRATIVE EMBODIMENT III

A mixture of 9.0 g (0.02 mole) of spirodilactam bis-ethyl benzoate of Embodiment I above or its corresponding diacid, 1.32 g (0.02 mole) of hexamethylene diamine, 2 drops of triethylamine and 25 ml of diglyme was heated at 170°-180° C. in a nitrogen atmosphere. Ethanol by-product was removed by distillation. After the reaction was complete, the reaction mixture was poured into methanol to isolate the polyamide polymer. Confirmation of the repeating polyamide unit was made by IR and $R^{13}$NMR spectral analyses.

ILLUSTRATIVE EMBODIMENT IV

A mixture of 0.01 mole of spirodilactam bis-benzoic acid of Embodiment I above, 0.01 mole of the diglycidyl ether of 2,2-(4-hydroxyphenyl)propane, a catalytic amount of an imidazole and 10 ml of diglyme is heated at 170°-180° C. in a nitrogen atmosphere. Ethanol by-product is removed by distillation. After the reaction is complete, the reaction mixture is poured into methanol to isolate the polyester polymer.

What is claimed is:

1. A polyester obtained by condensing a dicarboxyaryl-substituted spirodilactam with a dihydroxy compound, said polyester comprising (a) moieties derived from a spirodilactam compound, said compound having nitrogen atoms in the 1- and 6-positions of the spiro ring system and having a carboxy- or carboxyalkylaryl substituent on each spiro ring nitrogen atom, alternating with (b) moieties derived from a dihydroxy compound or a diepoxide compound.

2. The polyester according to claim 1 of the formula

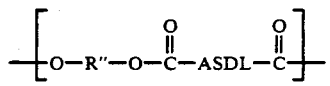

or

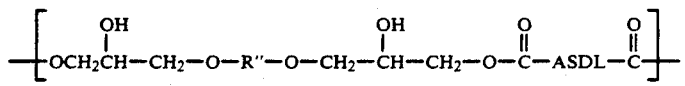

wherein ASDL is a moiety of an aryl- or alkylaryl-substituted 1,6-diaza[4.4]spirodilactam having aryl or alkylaryl substituents on each spiro nitrogen atom; and R" is an unsubstituted or inertly substituted aliphatic or aromatic group of up to 18 carbon atoms.

3. The polyester of claim 2 wherein the ASDL is represented by the formula

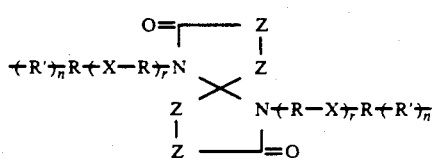

wherein Z independently is >C(Z')$_2$ in which Z' independently is hydrogen, lower alkyl of from 1 to 4 carbon atoms, halogen or phenyl or Z is such that two adjacent Z groups taken together form a ring system Z" of 1 to 3 rings, each ring having from 5 to 7 atoms, up top two of which are heteroatoms selected from nitrogen, oxygen or sulfur, there being up to 15 carbon atoms in each Z", two of which form a bridge between the carbon atoms connected by the adjacent Z groups; R is an aromatic group of up to 18 carbon atoms and up to two aromatic rings, inclusive; R' is R or an aliphatic group of up to 10 carbon atoms inclusive; n and r each independently is 0 or 1; X is a direct valence bond or X is alkylene of up to 8 carbon atoms inclusive, oxy, thio, sulfonyl, carbonyl, dioxyphenylene, 2,2-di(oxyphenyl)propane or dioxyphenylene.

4. The polyester according to claim 3 wherein R" is independently an alkylene group of 2 to 10 carbon atoms or an arylene group of 6 to 10 carbon atoms.

5. The polyester of claim 4 wherein each n and r is zero.

6. The polyester of claim 5 wherein Z is >C(Z')$_2$.

7. The polyester of claim 6 wherein Z' is hydrogen.

8. The polyester of claim 6 wherein R" is ethylene.

9. The polyester of claim 6 wherein R" is butylene.

10. The polyester of claim 6 wherein R" is biphenyl.

11. The polyester of claim 6 wherein R" is 2,2-di(-phenyl)propane.

12. The polyester of claim 3 wherein adjacent Z moieties are Z".

13. The polyester of claim 12 wherein R is phenylene.

14. The polyester of claim 13 wherein Z" is benzo.

15. The polyester of claim 14 wherein R is p-phenylene.

16. A polyamide obtained by condensing a derivative of a carboxyaryl-substituted spirodilactam with a primary diamine compound, said polyamide comprising (a) moieties derived from a spirodilactam compound, said compound having nitrogen atoms in the 1- and 6-positions of the spiro ring system and having a carboxy- or carboxyalkylaryl substituent on each spiro ring nitrogen atom, alternating with (b) moieties derived from a primary diamine compound.

17. The polyamide of claim 16 of the formula

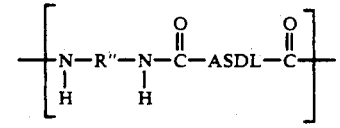

wherein ASDL is a moiety of an aryl or alkylaryl-substituted 1,6-diaza [4.4] spirodilactam having aryl or alkylaryl substituents on each spiro nitrogen atom and R" is an unsubstituted or inertly substituted aliphatic or aromatic group of up to 18 carbon atoms and up to two aromatic rings.

18. The polyamide according to claim 17 wherein ASDL is represented by the formula

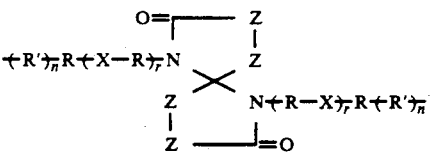

wherein Z independently is >C(Z')$_2$ in which Z' independently is hydrogen, lower alkyl of from 1 to 4 carbon atoms, halogen or phenyl or Z is such that two adjacent Z groups taken together form a ring system Z" of 1 to 3 rings, each ring having from 5 to 7 atoms, up to two of which are heteroatoms selected from nitrogen, oxygen or sulfur, there being up to 15 carbon atoms in each Z", two of which form a bridge between the carbon atoms connected by the adjacent Z groups, R is an aromatic group of up to 18 carbon atoms and up to two aromatic rings, inclusive; R' is an aliphatic group of up to 10 carbon atoms, inclusive; n or r each independently is zero or 1; X is a direct valence bond or X is alkylene of up to 8 carbon atoms, inclusive, oxy, thio, sulfonyl, carbonyl, dioxyphenylene, 2,2-di(oxyphenyl)propane or dioxydiphenylene.

19. The polyamide according to claim 18 wherein R″ is independently an alkylene group of 2 to 10 carbon atoms or an arylene group of 6 to 10 carbon atoms.

20. The polyamide of claim 19 wherein each n and r is zero.

21. The polyamide claim 20 wherein Z is >C(Z′)$_2$.

22. The polyamide of claim 21 wherein each Z′ is hydrogen.

23. The polyamide of claim 21 wherein R″ is hexamethylene.

24. The polyamide of claim 22 wherein R″ is methylenediphenyl.

25. The polyamide of claim 20 wherein adjacent Z groups are Z″.

26. The polyamide of claim 25 wherein Z″ is benzo.

* * * * *